United States Patent [19]

Uchiyama et al.

[11] 4,209,257
[45] Jun. 24, 1980

[54] APPARATUS FOR DETECTING DEFECTS IN PATTERNS

[75] Inventors: Yasushi Uchiyama, Yokohama; Daikichi Awamura, Kawasaki, both of Japan

[73] Assignee: Nippon Jidoseigyo Ltd., Kawasaki, Japan

[21] Appl. No.: 922,216

[22] Filed: Jul. 5, 1978

[30] Foreign Application Priority Data

Jul. 15, 1977 [JP] Japan .................................. 52-84056

[51] Int. Cl.$^2$ ............................................. G01B 11/00
[52] U.S. Cl. ..................................... 356/394; 356/398
[58] Field of Search ........................... 356/71, 394, 398

[56] References Cited

U.S. PATENT DOCUMENTS

| | | | |
|---|---|---|---|
| 3,546,377 | 12/1970 | Troll | 356/398 |
| 4,123,170 | 10/1978 | Uchiyama et al. | 356/398 |

*Primary Examiner*—John K. Corbin
*Assistant Examiner*—R. A. Rosenberger
*Attorney, Agent, or Firm*—Stevens, Davis, Miller & Mosher

[57] ABSTRACT

An apparatus for detecting defects in patterns, particularly defects in chip patterns of photomasks for use in manufacturing semiconductor integrated circuits comprising optically scanning means for scanning in a raster scan mode identical portions of the two patterns to be compared with each other by means of a pair of lens systems to produce a pair of picture signals each corresponding to a respective one of the scanned pattern portions and a defect signal producing means for receiving said pair of picture signals and producing a defect signal as a difference between the two picture signals. A variable delay circuit is provided between the optically scanning means and defect signal producing means to correct or compensate for deviations in the two picture signals due to differences in optical characteristics between the two lens system such as distortion and magnification. The variable delay circuit delays the picture signals for a delay time which is varied as a function of a position on the raster.

22 Claims, 18 Drawing Figures

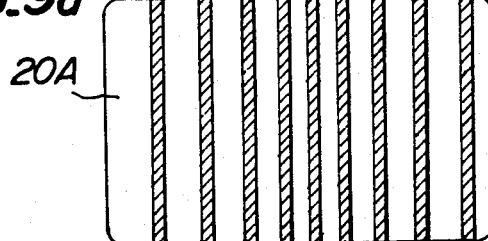
FIG.9a
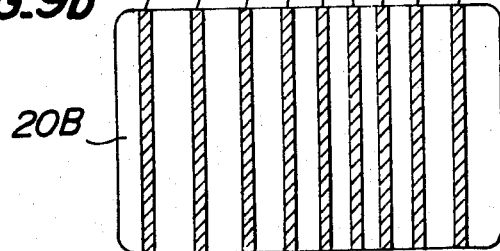
FIG.9b
FIG.10
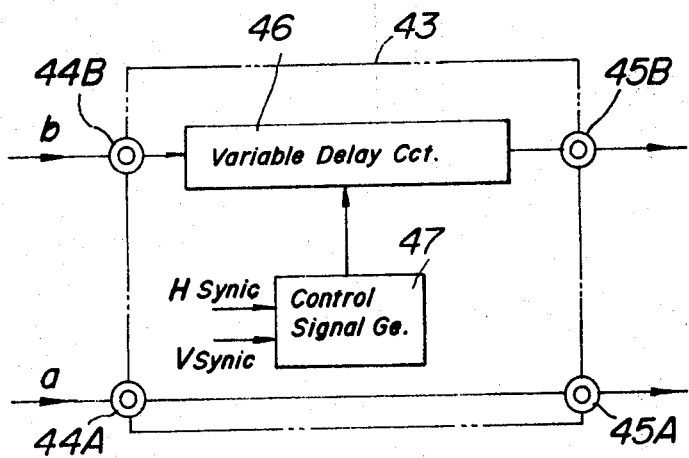

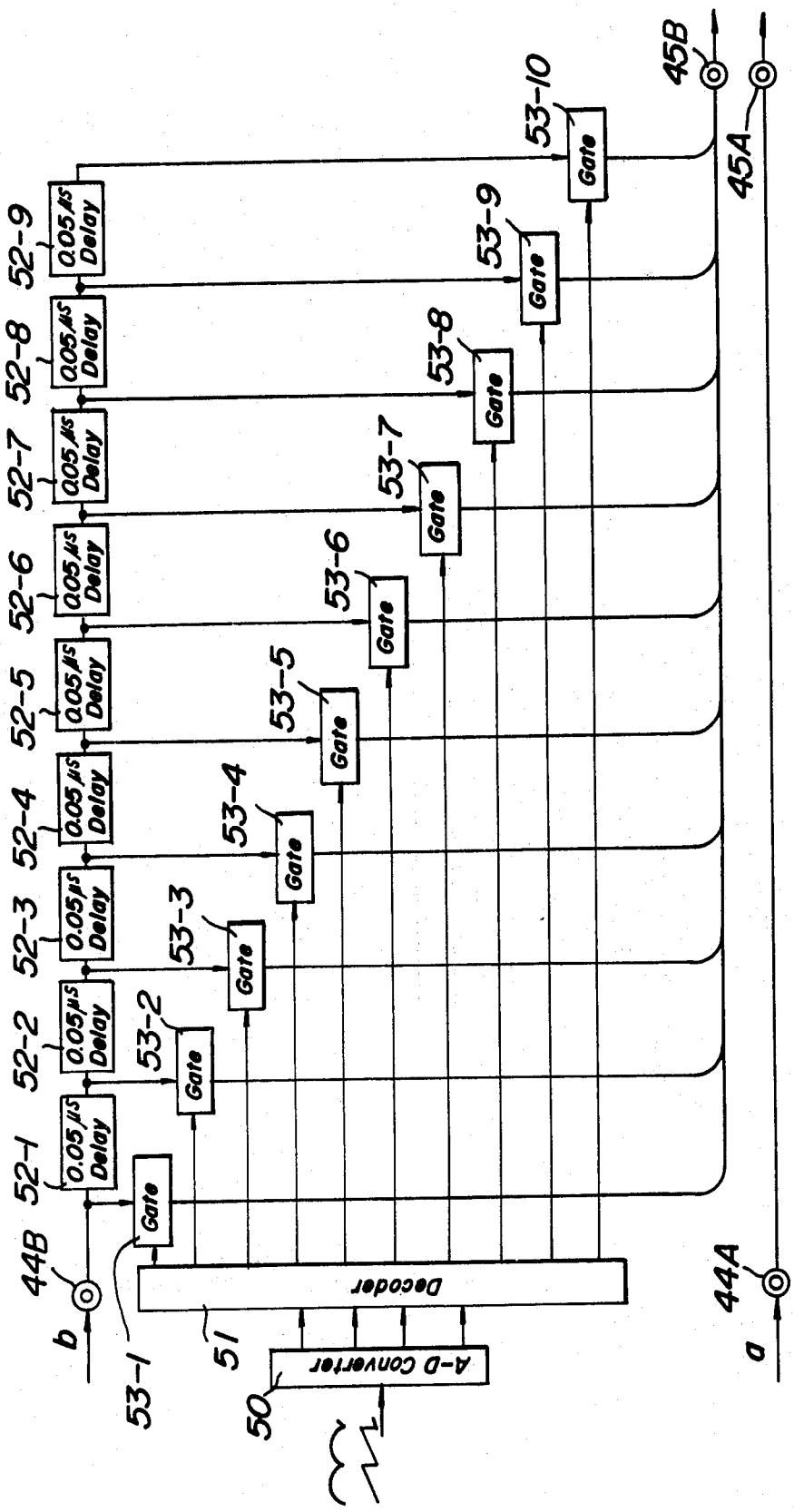

APPARATUS FOR DETECTING DEFECTS IN PATTERNS

BACKGROUND OF THE INVENTION

1. Field of the Invention

The invention relates to an apparatus for detecting defects in patterns, particularly defects in chip patterns of photomasks for use in manufacturing semiconductor integrated circuits.

2. Description of the Prior Art

In processes of manufacturing integrated circuits there is a process for photoetching a silicon wafer. In this process a mask having a desired pattern is placed on a photo-lacquer layer applied on the silicon wafer and the photo-lacquer layer is irradiated by visible light or an ultraviolet ray through the mask. Then the silicon wafer is selectively photoetched in accordance with the mask pattern. The defects in the mask having the pattern printed thereon might affect the yield of the manufactured integrated circuits. The mask is formed by depositing a metal film such as chromium on a glass plate having a sufficiently flattened surface and then by printing a desired pattern on the surface. If there are pin holes in the metal film, the printed pattern might have defects. The present inventors have developed an apparatus for detecting automatically such pin holes in the metal film of the mask pattern with high accuracy.

The photomask has various defects in its pattern as well as the pin holes. The defect detecting apparatus according to the present invention is particularly suitable to detect such defects in the printed pattern of the photomask.

FIG. 1 shows schematically a photomask 1 which is used for manufacturing semiconductor integrated circuits. In the mask 1 there are formed a number of identical chip patterns 3 which are divided by a number of orthogonal scribe lines 2.

FIG. 2 is a microscopic image of a part of the chip pattern 3. This part of the pattern has no defect and thus is a perfect one. The pattern is composed of transparent portions 4 and opaque portions 5. FIG. 3 is also a microscopic image of the corresponding part of another pattern which includes various defects. Portions A and B are residual parts of the metal film. At the portion A the residual part bridges two adjacent lands which should be separated from each other. Thus this residual portion A should be detected as a real or true defect. The other residual portion B exists in a space and in most cases this portion B might not injure the integrated circuits. At a portion C a part of a land is lacking. However, this land is not completely separated and thus this portion C might not affect the integrated circuits. At a portion D a land is completely cut away and this causes a serious adverse influence on the integrated circuits.

Up to now there have been developed the following methods have been developed for detecting the above mentioned defects in the mask pattern.

(1) The mask is inspected by means of a microscope so as to find the defects. In general the pattern is formed by straight lines which intersect perpendicularly with each other, while most defects have irregular shapes as shown in FIG. 3. Therefore the defects can be found in a relatively easy manner. However, this method requires a lot of time and labor and thus is not suitable for detecting the defects in the photomask used in manufacturing the integrated circuits which have a number of chip patterns.

(2) As shown in FIG. 4 a sample mask 7 which has a perfect pattern is prepared and images of this sample mask 7 and the mask 6 to be tested are inspected in a superimposed manner. In this case the image of the mask 6 to be tested is colored in red and the image of the sample mask 7 is colored in green which is complementary to red. For this purpose there is arranged a red color light source 9 and the mask 6 to be tested is irradiated by red light emitted from the source 9. The red light passing through the mask 6 is made incident on an inspection eye 14 by means of an objective 10, a mirror 11, a half mirror 12 and an eye piece 13. The sample mask 7 is illuminated by a green light source 15 and the green light passing through the sample mask 7 is made incident upon the inspection eye 14 by means of an objective 16, a mirror 17, a half mirror 18 and the eye piece 13. When the sample mask 7 having no defect as shown in FIG. 2 and the test mask 6 having the defects as illustrated in FIG. 3 are inspected in a superimposed manner, the portions A and B are seen in green, because in these portions only the green light from the sample mask 7 reaches the inspection eye 14. The portions C and D are seen in red, because in these portions only the red light from the mask 6 reaches the eye 14. The transparent portion other than the portions A, B, C and D can be seen in white, because in the transparent portion both the green and red light rays from the masks 6 and 7, respectively reach simultaneously the inspection eye 14. The opaque portion 5 is seen, of course in black. The defect portions are seen in green or red and the portions having no defect are seen in black or white. Thus the defects can be found in a simpler manner. The masks used in manufacturing the integrated circuits have formed therein a number of identical chip patterns and in order to check such a mask it is necessary to arrange the mask 6 to be tested and the sample mask 7 on a same carrier stage 19 and to move this carrier stage 19 slightly so as to check the successive chip patterns. In case of inspecting the two images of the masks 7 and 6 in the superimposed manner two images must be aligned accurately. If there is an error in this alignment it is impossible to detect the defects accurately. In particular when the two masks 6 and 7 are placed on the same table 19, the masks must be aligned with X and Y directions of the movement of the table. If there is an error in this alignment, the error in superimposition of the two images will increase in accordance with the movement of the table 19. A play in the carrier table 19 also affects the superposition of the two images. Morever since this method is effected with the naked eye, the inspector might be tired causing human errors which cannot be avoided. Also, a long time period is required for inspection.

(3) Electric signals corresponding to a sample pattern which does not include a defect have been previously stored in a record medium such as a magnetic tape or memory elements using an electronic computer. The image of the mask to be tested is picked up by means of a microscopic television camera to produce a video signal. This video signal is compared with the previously stored signal of the sample pattern so as to detect the defects in the checked mask. This method has an advantage in that the defects can be detected automatically without using a visual inspection. However an apparatus for carrying out such a method is liable to be very large and complicated in construction and thus the apparatus becomes quite expensive.

In order to avoid the disadvantages mentioned above the inventors have designed an apparatus comprising a single camera tube on which images of identical portions of two patterns to be checked are focussed in a superimposed manner and defects in the patterns are detected by detecting an amplitude of the output video signal from the camera tube. In this apparatus the defects are represented as gray tones in the video signal and the gray tones are detected by means of an amplitude limiter. However the accuracy of the defect detection was low, because the fluctuation of the amplitude of the video signal is large. In order to obviate this disadvantage the inventors have further developed a method in which use is made of two camera tubes on each of which a respective image of the two patterns is formed and defects in the patterns are detected by comparing two output video signals from the two camera tubes. In this method the accuracy of the defect detection is a greatly improved as compared with the method in which only the single camera tube is used. However it has been found that it is quite difficult to make two camera tubes operate identically. Moreover in case of using the camera tube the carrier table on which the masks to be compared are placed must be transported intermittently due to the residual image effect of the camera tube. This results in a very complicated driving mechanism for the carrier table. The operation speed of the camera tube is rather slow and a time period of 70 to 100 ms is required for checking each field of view. Therefore a quite long time is required for detecting the defects in a number of patterns of the mask.

The inventors have further devised a checking apparatus which can avoid all of the above mentioned drawbacks and check the defects in patterns accurately and speedily with a simple construction. This apparatus comprises means for producing a scanning light spot, an optical system for directing the spot onto two identical portions of patterns to be compared with each other, a pair of light receiving devices each receiving a light transmitted through or reflected from respective pattern portions, circuit means for inverting a phase of an output signal supplied from one of said two light receiving devices and circuit means for mixing the phase inverted output signal and a non-inverted output signal from the other light receiving device. According to such an apparatus the adjacent patterns 3 formed in the photomask 1 shown in FIG. 1 for use in manufacturing the integrated circuits can be compared with each other and defects can be detected with high accuracy. After various experiments it has been further found that the pattern might be detected as having defects even when the relative position of two patterns to be compared with each other deviates slightly and/or these patterns differ from each other only slightly. This results in that masks are unnecessarily rejected as defective masks. That is to say the slight deviation of patterns and/or slight differences in patterns are detected as defects even if they do not affect the manufacture of integrated circuits and thus such masks should not be identified as defective.

The reasons for producing the above mentioned pseudo-defects may be summarized as follows:

(1) A pair of lens systems for forming two images of two patterns to be compared have different distortion characteristics.

(2) A stage for carrying the mask having the patterns to be compared rotates slightly during its travel causing the two images to deviate slightly with respect to each other.

(3) A distance or pitch between the successive chips has an error (about 0.5 $\mu$m) due to inaccuracy of a repeater used in manufacturing the photomasks.

(4) Contours of the pattern images fluctuate due to noise in the picture signals.

(5) If the glass plate of the photomask has less plainness, the two lens systems cannot be simultaneously focussed correctly.

Among the above mentioned causes the first and third ones are important or serious. But the problem with respect to the repeater has been improved because nowadays fine patterns have been required and the deviation in chip pitch can be made very small.

The inventors have further devised an improved checking apparatus which can effectively remove the pseudo-defects which should not be detected as true defects. This apparatus is disclosed in U.S. patent application Ser. No. 746,584 filed on Dec. 1, 1976 now U.S. Pat. No. 4,123,170

This apparatus comprises a pattern scanning device for scanning optically identical portions of two patterns to be compared with each other to produce corresponding picture signals, circuit means for subtracting one of the picture signal from the other picture signal to produce a difference signal denoting pattern differences, delay means for delaying the difference signal and circuit means for receiving said delayed difference signal and the non-delayed difference signal to produce an output defect signal in which any pseudo-defects having dimensions smaller than a given dimension determined by the delay time have been removed.

According to the last mentioned defect detecting apparatus as far as a vicinity of the contour of pattern is concerned patterns are compared with each other after their contours have been thinned by a predetermined length and thus the slight registration error and the small defects at the contours can be ignored.

It has been found that when the defects in the patterns are detected by means of such an apparatus in which the pseudo-defects in the vicinity of the pattern contours are removed, it is necessary to increase the width of the contour regions if the two lens systems of the scanning means have differences in characteristics such as distortion and magnification, and thus the defect detection sensitivity is naturally decreased. In other words it is impossible to utilize the maximum resolution of the whole apparatus including the optical system and electric circuitry and the effective resolution becomes very low. In order to decrease the distortion of the lens system it is necessary to use very complicated and expensive lens systems. It should be noted that the scanning means comprise a pair of lens system which simultaneously project the scanning light spots onto the identical pattern portions, the differences in distortion and/or magnification between the two lens systems result in the registration error of the two scanned pattern portions, which error might be detected as a defect.

SUMMARY OF THE INVENTION

The invention has for its object to provide an improved defect detecting apparatus in which the decrease of the defect detection sensitivity due to difference in distortion and/or magnification can be compensated electrically.

According to the invention an apparatus for detecting defects in patterns comprises means including first and second lens systems each of which projects a light spot onto a respective one of two identical portions of two patterns to be compared with each other and for scanning said portions in a raster scanning mode to produce first and second picture signals corresponding to said two portions, respectively;

delay means for delaying at least one of said first and second picture signals for a delay time which is varied as a function of a position on the raster so as to decrease a relative deviation of the picture signals mainly due to a difference in distortion and/or magnification between the first and second lens systems;

means for receiving output picture signals from said delaying circuit and forming a difference between the first and second picture signals to produce a defect signal.

BRIEF DESCRIPTION OF THE DRAWINGS

FIGS. 9a and 9b are schematic views of a monitor screen for illustrating the deviation of pattern portions;

FIG. 10 is a circuit diagram of an embodiment of a deviation correcting circuit according to the invention;

FIG. 12 is a block diagram showing an embodiment of a variable delay circuit of the correcting circuit;

DESCRIPTION OF THE PREFERRED EMBODIMENTS

Figure 5:
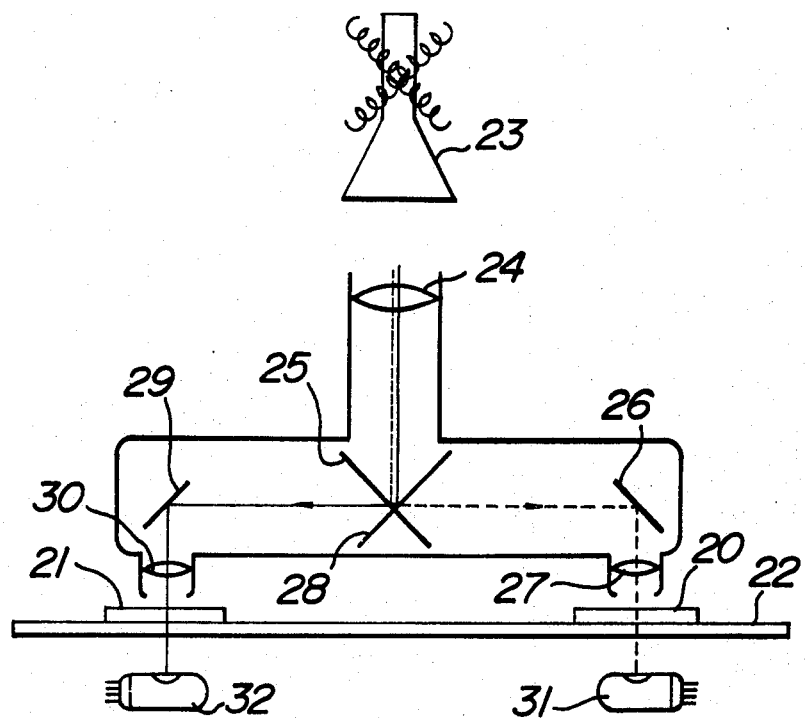
FIG. 5 is a schematic view showing an embodiment of an optical system of a defect detecting apparatus according to the invention.

FIG. 5 shows diagrammatically an embodiment of an optically scanning system of a defect detecting apparatus according to the invention. In this embodiment a mask 20 to be tested and a sample mask 21 having no defect are placed on a single carrier table 22. A flying spot cathode ray tube 23 is provided and an image of a scanning raster formed by the flying light spot is focussed on the mask 20 by means of a lens 24, a half mirror 25, a mirror 26 and a first lens 27 and on the mask 21 by means of the lens 24, a half mirror 28, a mirror 29 and a second lens 30. The light passing through the mask 20 is received by a first photo-electric converter 31 and the light passing through the mask 21 is received by a second photoelectric converter 32. In this case the raster image of the flying spot scanner 23 should be projected on identical pattern portions of the masks 20 and 21. Therefore if the mask 20 does not include a defect in the related pattern portion, the electric output signals from the photoelectric converters 31 and 32 are identical with each other. But if the mask 20 has a defect, the two output signals are different from each other. Therefore by comparing these output signals the defects in the pattern on the mask 20 can be detected with the high accuracy.

In the above embodiment since the mask 20 and the sample mask 21 are placed on the same carrier table 22 and are moved in the orthogonal X and Y directions, the two masks have to be aligned accurately in the X and Y directions. If the two masks 20 and 21 are not aligned correctly or the carrier table 22 has a play, the scanned pattern portions of the masks 20 and 21 become different from each other with the movement of the carrier table 22 and thus accurate defect detection can not be effected.

Figure 6:
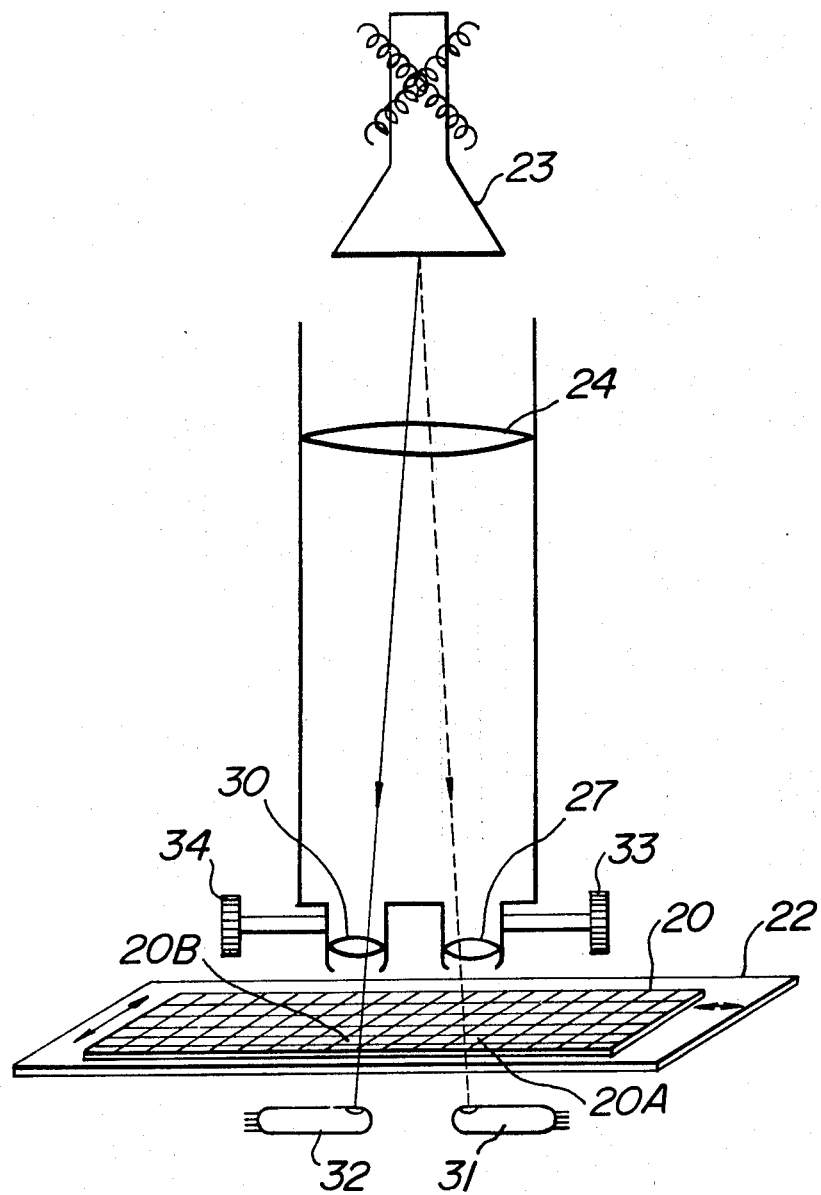
FIG. 6 is a schematic view illustrating another embodiment of the optical system of the defect detecting apparatus according to the invention.

FIG. 6 shows another embodiment of the optically scanning system of the defect detecting apparatus according to the invention. In this embodiment the disadvantage just mentioned above can be deleted. In FIG. 6 the same elements as those shown in FIG. 5 are denoted by the same reference numerals. In FIG. 6 only the mask 20 to be checked is placed on the carrier table 22. A scanning raster image of the flying spot scanner tube 23 is focussed on a part of a pattern 20A of the mask 20 by means of a common lens 24 and a first lens 27 and on a corresponding part of a pattern 20B which is near the pattern 20A by means of the common lens 24 and a second lens 30. In order to inspect the identical portions of the patterns 20A and 20B a distance between optical axes of the lenses 27 and 30 can be adjusted by means of adjusting handles 33 and 34. In the present embodiment the accuracy of the defect detection is little affected by the play of the carrier table 22, because the two patterns 20A and 20B situated quite close together.

In the above mentioned optically scanning systems the scanning light spot is simultaneously projected onto the identical pattern portions by means of the two lens systems 27 and 30. In general these lens systems 27 and 30 have differences in characteristics such as distortion and magnification and thus the picture signals simultaneously obtained by scanning the two pattern portions deviate relative to each other.

Figure 3:
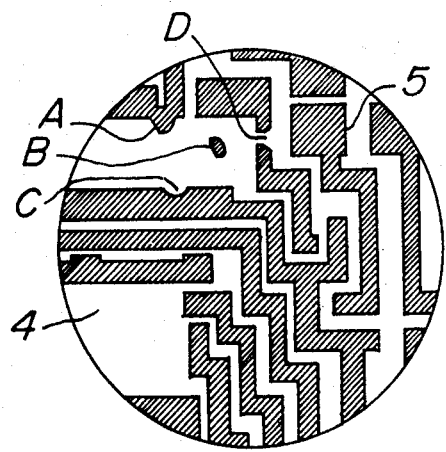
FIG. 3 is also a microscopic image of the same part of a photomask which includes various defects.
Figure 4:
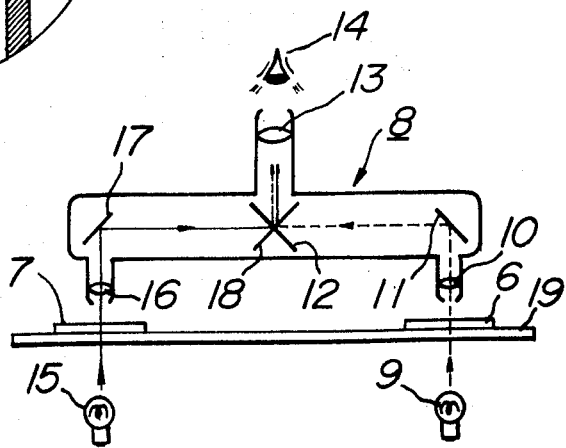
FIG. 4 is a schematic view illustrating a known defect detecting apparatus.
Figure 7:
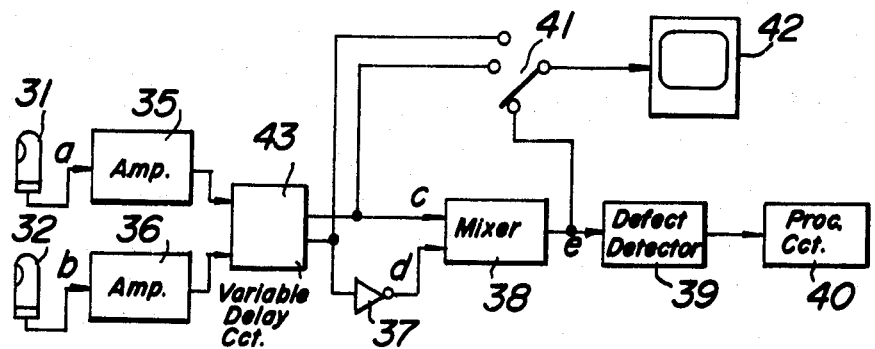
FIG. 7 is a block diagram showing an embodiment of electric circuit means of the defect detecting apparatus according to the invention.
Figure 8:
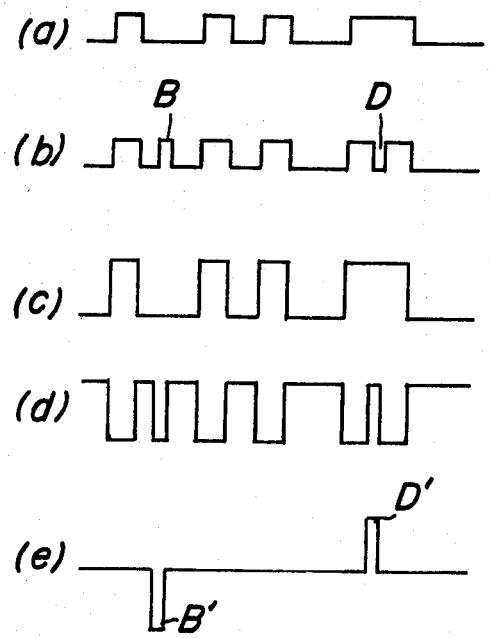
FIGS. 8a to 8e are waveforms for explaining the operation of the circuit means of FIG. 7.

FIG. 7 is a block diagram illustrating an embodiment of the defect detecting apparatus according to the invention. FIG. 8 illustrates waveforms at various points of the circuit of FIG. 7 FIG. 8a shows a waveform of an output signal from the first photoelectric converter 31 which receives the scanning light spot passing through the pattern 20A and FIG. 8b illustrates a waveform of an output signal from the second photoelectric converter 32 which receives the scanning light spot passing through the pattern 20B. It is now assumed that one of the patterns 20A does not include a defect, but the other pattern 20B has defects. A pulse B in the waveform of FIG. 8b is produced by the defect B shown in FIG. 3 and a pulse D corresponds to the defect D in FIG. 3. The first picture signal supplied from the first photoelectric converter 31 is amplified by an amplifier 35. The second picture signal from the second photoelectric converter 32 is also amplified by an amplifier 36. These picture signals are supplied to a deviation correcting circuit 43. The second picture signal is further inverted by an inverter 37. The first picture signal (FIG. 8c) and the inverted second picture signal (FIG. 8d) are supplied to a defect signal producing circuit 38. An output signal from the circuit 38 is shown in FIG. 8e. As shown in the drawing the level of the output signal corresponding to portions with no defect appears as a zero level, but the signal level differs from zero at portions of defects, so that defect pulses B' and D' are produced. These defect pulses B' and D' have opposite polarities. These pulses are supplied through a slicer 39 to a defect detection and process circuit 40. The output defect signal from the defect signal producing circuit 38 may be supplied to a monitor 42 through a switch 41 so as to inspect the condition of superimposition of the two patterns 20A and 20B. That is the user can adjust the handles 33 and 34 while inspecting the superimposed images of the patterns 20A and 20B on the monitor 42 and the two images can be registered completely. Moveover in order to inspect in detail any one of the images of the patterns 20A and 20B, any one of the output signals from the amplifiers 35 and 36 may be supplied to the monitor 42 through the switch 41.

Figure 1:
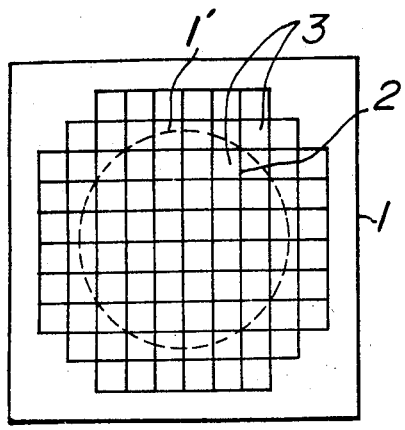
FIG. 1 is a plan view showing a photomasks used for manufacturing integrated circuits.
Figure 2:
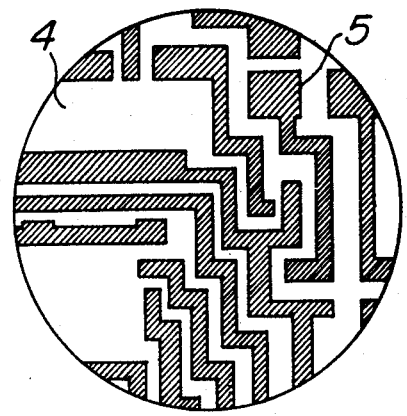
FIG. 2 is a microscopic image of a part of a photomask which does not include any defect.

In the embodiment shown in FIG. 6 the two patterns 20A and 20B of the same mask 20 to be checked are compared with each other. This is based on the fact that the mask has a number of identical patterns and the probability that the same defects exist in these patterns is very small, and thus the defects can be detected very accurately without using the sample mask having the perfect patterns. In this method the number of the comparisons of the patterns situated near the peripheral portion of the mask is small and the detection accuracy for these peripheral patterns might be reduced. However, in general only the patterns in the mask which are enclosed by a dotted circle 1' in FIG. 1 are used in manufacturing the semiconductor integrated circuits, and the peripheral patterns are not used. Thus there is no serious problem.

In the above embodiment of the signal representing the pattern 20B (FIG. 8d) is subtracted from the signal representing the pattern 20A (FIG. 8c). In addition to this the latter signal of FIG. 8c may be subtracted from the former signal of FIG. 8d so as to produce pulse signals having the opposite polarity to that shown in FIG. 8e. These two pulse signals are supplied to a rectifying circuit to produce a pulse signals having, for example a positive polarity. When such a pulse signal is supplied to the monitor 42, the defects are displayed as white images on the monitor screen. Instead of such a measure the pulse signal of FIG. 8e may be supplied to a full-wave rectifying circuit.

In the explanation hereinbefore it is assumed that the defects have relatively large areas and should be detected as true defects. In the practical defect detection process, there are produced a number of very small defects, particularly pseudo-defects owing to the deviation of the first and second picture signals due to difference in distortion and/or magnification between the first and second lens systems 27 and 30. According to the invention such deviation in the picture signals is to be effectively removed by means of the deviation correcting circuit 43.

FIGS. 9a and 9b show monitor screens displaying the two pattern images 20A and 20B, respectively. As can be seen from these figures the displayed patterns are relatively shifted in the horizontal direction due to the difference in the distortion between the two lens systems (for example the lens systems 27 and 30 in FIG. 6). That is to say in the middle portion of the frame there is little deviation, but the deviation becomes larger toward the edges of the frame and further the direction of the deviation is opposed to each other on left and right sides. When such a deviation is produced, the large pseudo-defects are detected even if the patterns have no true defect and the reliability of the defect detecting apparatus might be lost. According to the invention the above mentioned deviation of the picture signals is corrected by passing at least one picture signal through a variable delay circuit whose delay time is varied in accordance with a position on the raster. For instance the delay time may be changed as a function of substantially parabolic form during the horizontal line scanning period.

FIG. 10 is a block diagram showing an embodiment of the deviation correcting circuit 43. In this embodiment the distortion characteristics of the lens system 30 of the optically scanning device shown in FIG. 6 is matched to the distortion characteristics of the other lens system 27. To this end the first picture signal a obtained by scanning the pattern 20A is directly transmitted from an input terminal 44A to an output terminal 45A. That is to say the picture signal a passes through the circuit 43 without being delayed. On the other hand the other picture signal b derived by scanning the other pattern 20B is supplied to a variable delay circuit 46 through an input terminal 44B and the delayed picture signal is supplied to an output terminal 45B. There is further provided a delay time control circuit 47 which receives horizontal and vertical synchronizing signals Hsync. and Vsync. of the picture signal and supplies a control signal to the variable delay circuit 46 to change the delay time as a function of position on the horizontal scan line of the raster as viewed in the horizontal direction.

Figure 11:
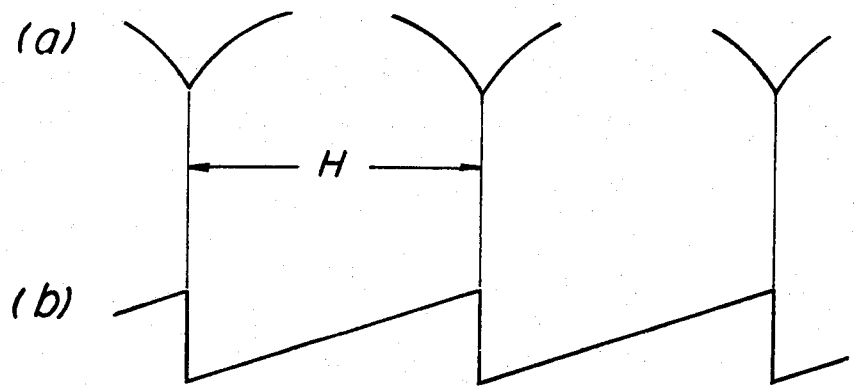
FIGS. 11a and 11b are waveforms of correction signals.

The deviation as shown in FIGS. 9a and 9b can be compensated by changing the delay time in a parabolic manner during the horizontal scanning period. Therefore the control circuit 47 generates a parabolic signal having a repetition period equal to the horizontal scanning period H as illustrated in FIG. 11a. For example the variable delay circuit 46 may be formed by a pi($\pi$)-type circuit network of inductors and variable capacitance diodes and the delay time can be changed in a desired manner by applying the parabolic control voltage signal to the variable capacitance diodes. In this manner the deviation of the two picture signals due to the distortion of the lens systems of the optically scanning device can be effectively compensated for and thus the pseudo-defects due to the relative deviation of the two picture signals can be effectively removed.

Further if there is a difference in magnification between the two lens systems, the picture signals are also subjected to the relative deviation and thus the pseudo-defects might be detected. In order to correct such a difference in magnification a sawtooth shape control signal as illustrated in FIG. 11b is produced by the control circuit 47 and this control signal is applied to the variable delay circuit 46 together with the parabolic control signal of FIG. 11a. In this manner the deviation of the picture signals due to difference in both distortion and magnification between the two lens systems can be compensated for and accurate defect detection can be performed while removing pseudo-defects.

FIG. 12 is a block diagram illustrating an embodiment of the variable delay circuit 46. In this embodiment the delay time control signal supplied from the control circuit 47 is first converted into a digital signal of four bits by an analog to digital converter 50 and the converted digital signal is further supplied to a decoder 51. The picture signal b received at the input terminal 44B is passed through nine delay circuit elements 52-1 to 52-9 each having a delay time of a fraction of the horizontal scanning period, e.g. 0.05 micro seconds. Further the nondelayed picture signal b is supplied to a gate 53-1 and output signals from the delay elements 52-1 to 52-9 are supplied to gates 53-2 to 53-10, respectively. To control input terminals of the gates 53-1 to 53-10 are connected respective output terminals of the decoder 51 and output terminals of these gates are commonly connected to the picture signal output terminal 45B.

In accordance with an instantaneous amplitude of the superimposed parabolic and sawtooth control signal supplied from the control circuit 47 the decoder 51 produces an output signal at a given output terminal e.g. a third output terminal counted from the top and then the gate e.g. gate 53-3 which is connected to said output terminal of the decoder 51 is relatively made conductive. Then the picture signal delayed by the delay elements 52-1 and 52-2 for $0.05 \times 2 = 0.1$ $\mu s$ is supplied to the output terminal 45B. In this manner the picture signal b can be delayed in a digital mode by a given time period which varies as a function of a position on the horizontal scanning line.

As shown in FIG. 6 the two lens systems 27 and 30 of the optically scanning device are arranged side by side in the horizontal scanning direction and thus the difference in distortion in the horizontal directions becomes relatively large, but in the vertical direction the deviation is rather small. Therefore in some applications it is sufficient to perform the correction with respect to the distortion only in the horizontal direction. Of course if the large difference in distortion between the two lens systems in the vertical direction is also produced, it is necessary to carry out the correction also in the vertical direction as explained in detail hereinafter.

Figure 13:
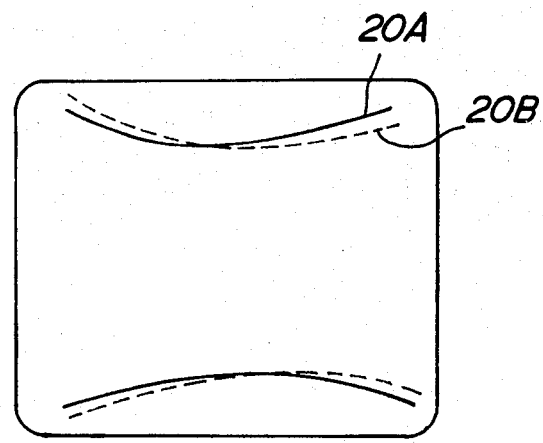
FIG. 13 is a schematic view of a monitor screen for showing a vertical deviation of the patterns.

FIG. 13 shows the monitor screen displaying the two picture signals of the two patterns 20A and 20B which are relatively deviated in the vertical direction. A solid line denotes the image of the pattern 20A and a broken line the image of the pattern 20B. Such a deviation produces the pseudo-defects which should not be detected as the real defect. According to the invention such a deviation can be corrected by delaying either one of the picture signals by a delay time which changes in accordance with the position on the raster.

Figure 14:
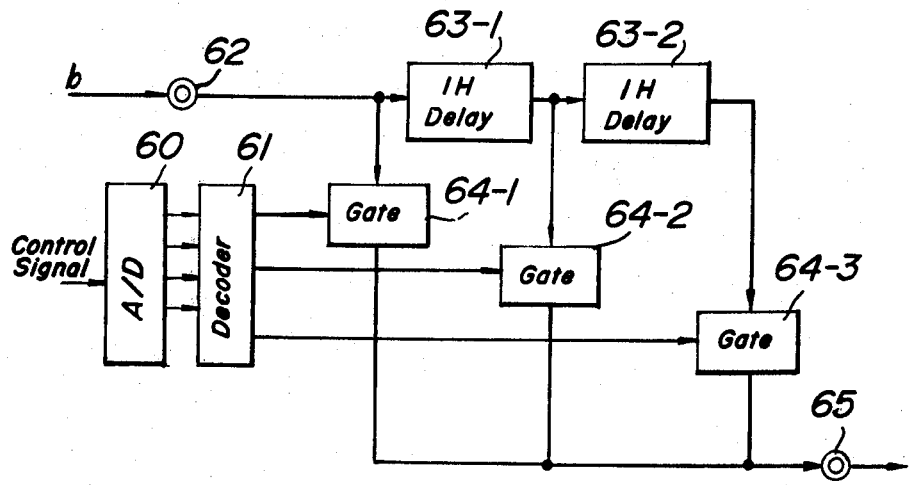
FIG. 14 is a block diagram showing an embodiment of a variable delay circuit of a vertical deviation correcting circuit.

FIG. 14 is a block diagram illustrating an embodiment of a variable delay circuit for correcting the above mentioned deviation in the vertical direction. In order to compensate the vertical distortion as shown in FIG. 13 use may be made of a control signal illustrated in FIG. 15a. This control signal has an amplitude which varies in a sawtooth manner at the horizontal scanning period H during the vertical scanning period V so as to change the delay time at a unit period of the horizontal scanning period H during the vertical scanning period V. This control signal is supplied to the vertical distortion correcting circuit of FIG. 14. In this circuit the control signal is converted into a digital signal of four bits by means of an analog-digital converter 60 and the converted digital signal is supplied to a decoder 61. The picture signal b to be delayed is supplied to an input terminal and is further supplied successively to delay elements 63-1 and 63-2 each having a delay time of one horizontal scanning period H. The nondelayed picture signal b is supplied to a gate 64-1 and 1H and 2H delayed picture signals are supplied to gates 64-2 and 64-3, respectively. The control input terminals of the gates 64-1, 64-2 and 64-3 are connected to output terminals of the decoder 61, respectively. The output terminals of the gates 64-1, 64-2 and 64-3 are commonly connected to a picture signal output terminal 65.

The decoder 61 produces an output at a given one of its three output terminals depending on an instantaneous amplitude of the control signal supplied to the analog-digital converter 60. Then the gate having its control input connected to said given output terminal is made conductive. Thus at the output terminal 65 there is obtained either one of the non-delayed, 1H delayed and 2H delayed picture signals. In this manner the picture signal b can be delayed at a unit period of H in accordance with the position on the raster and thus the difference in distortion in the vertical direction between the two lens systems can be compensated.

Figure 15:
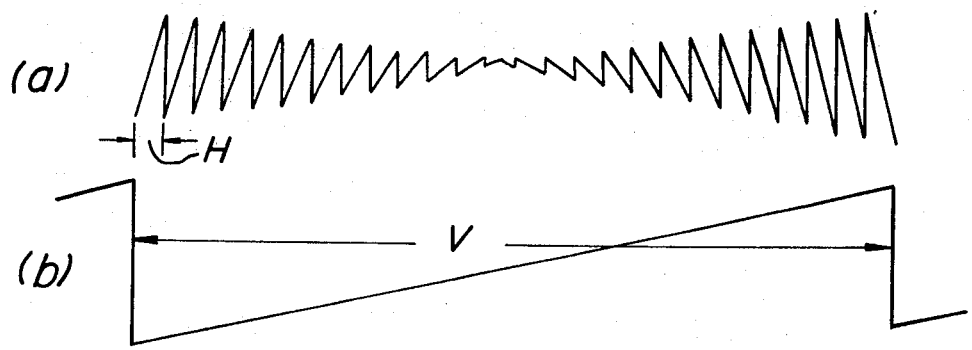
FIGS. 15a and 15b are waveforms of vertical deviation correcting signals.

Also in the vertical direction the deviation of the two picture signals due to the difference in magnification of the two lens systems may be corrected. For this purpose one can use a control signal having a sawtooth waveform as shown in FIG. 15b with superimposed it on the control signal of FIG. 15a.

Figure 16:
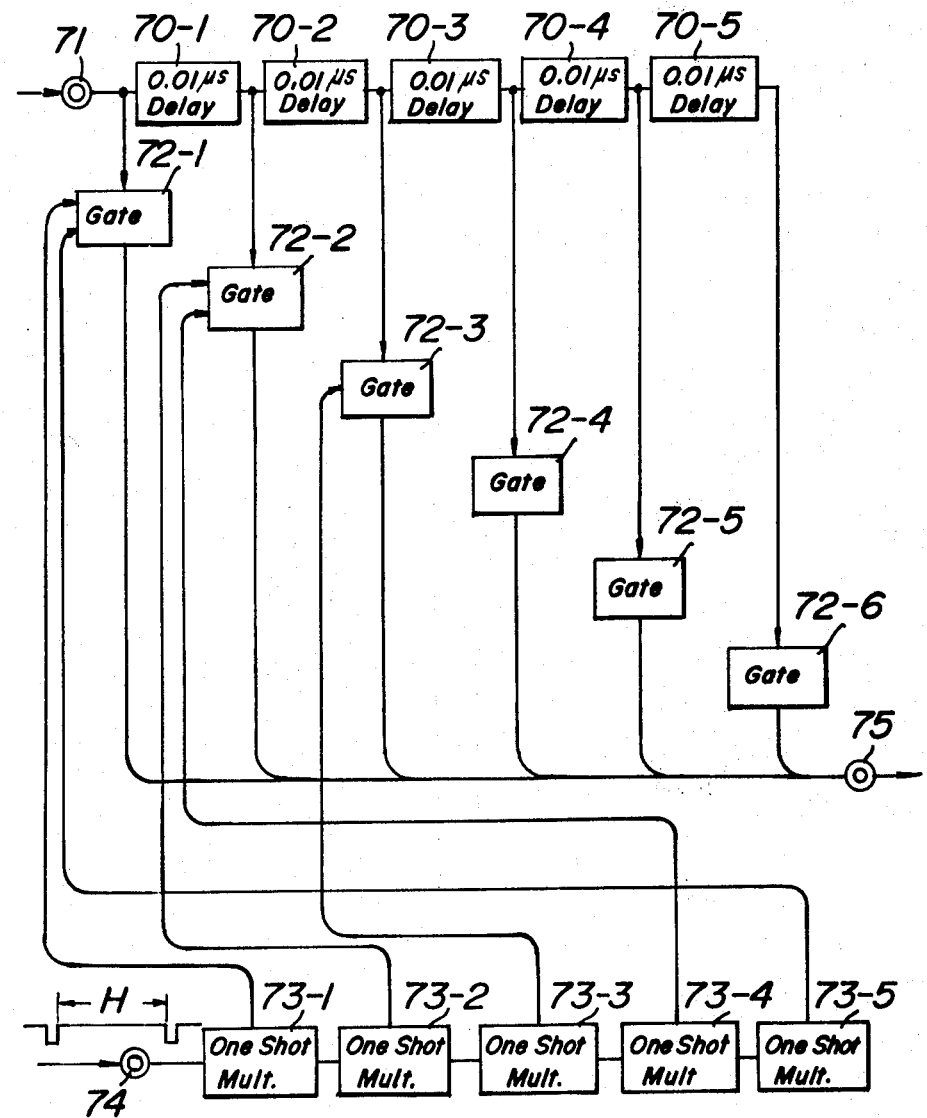
FIG. 16 is a block diagram of another embodiment of the variable delay circuit of the horizontal deviation correcting circuits.

FIG. 16 is a block diagram showing still another embodiment of the variable delay circuit which may be used for correcting the difference in distortion and/or magnification in the horizontal direction. According to the invention the registration error of the two pattern portions due to the different optical characteristics between the two lens systems of the optically scanning device can be corrected. This correction is only needed once during the manufacture and adjustment of the apparatus unless at least one of the lens systems will be replaced. Therefore in the present embodiment the delay time is not variable, but is half fixed. That is to say the delay time is made variable during the adjustemnt and after that the delay time is fixed.

Figure 17:
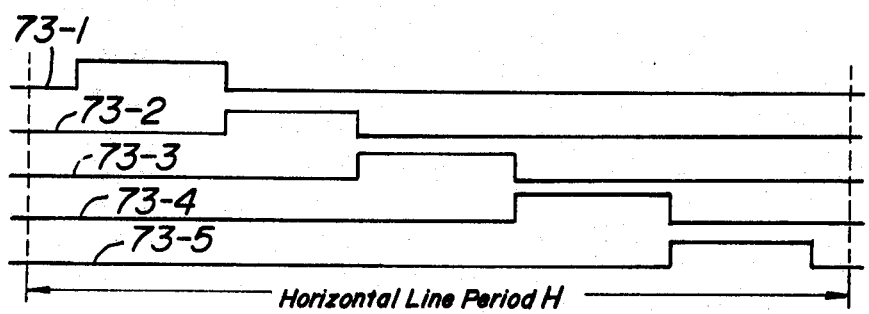
FIG. 17 shows waveforms for explaining the operation of the variable delay circuit of FIG. 16.

As illustrated in FIG. 16 there are provided five delay elements 70-1 to 70-5, each having a delay time of a fraction of the horizontal scanning period, e.g. 0.01 $\mu s$. Thus it is possible to obtain various delay times with a step of 0.01 $\mu s$ up to the maximum delay time of 0.05 $\mu s$. The maximum delay time is set to a such value that the predictable maximum distortion can be compensated. The picture signal is supplied from an input terminal 71 to the delay elements in succession. The non-delayed picture signal and successively delayed signals are supplied to gates 72-1 to 72-6, respectively. Output terminals of these gates are commonly connected to a picture output terminal 75. Further there are provided five one-shot multivibrators 73-1 to 73-5 connected in cascade to the input terminal 71, to which is supplied a trigger pulse having a repetition period of H through a terminal 75 from the control circuit so as to generate five pulses shown in FIG. 17 during the one line period H from the five multivibrators 73-1 to 73-5. In this manner the pulses are obtained which divide the one line period H into equal five fractions. The number of the multivibrators may be increased so as to divide the period H into more fractions.

During the adjustment of the apparatus the output pulses from the multivibrators 73-1 to 73-5 are supplied to control input terminals of various gates 72-1 to 72-6 so as to find an optimal condition in which the difference in distortion becomes minimum. Then the output terminals of the multivibrators are permanently connected to the control input terminals of the given gates by means of, for example, soldering. In the embodiment shown in FIG. 16 the multivibrators 73-1 and 73-5 are connected to the gate 72-1, the multivibrators 93-2 and 93-4 to the gate 72-2 and the multivibrator 73-3 to the gate 72-3. Therefore during a first fifth of the line period H, i.e. during a period in which the pulse shown in FIG. 17 by 73-1 is supplied from the first one-shot multivibrator 73-1, only the gate 72-1 is made conductive and thus the non-delayed picture signal is supplied to the output terminal 75. In the similar manner during the second 1/5 period of the line period H, only the gate 72-2 is made conductive and thus the picture signal delayed by 0.01 μs is fed to the output terminal 75. In this manner at the output terminal 75 it is possible to obtain the picture signal which has been delayed desirably in accordance with the positions on the horizontal line scan.

As explained above according to the defect detecting apparatus of the invention it is possible to correct or compensate the deviation of scanned pattern portions due to the difference in distortion and/or magnification of the two lens systems provided in the optically scanning device for scanning in the raster scan mode the two identical pattern portions to be compared with each other. Therefore it is possible to remove the pseudo-defects and thus the defect detection sensitivity can be materially increased, so that the reliability of the apparatus can be increased.

It should be noted that the present invention is not limited to the embodiments explained above and many modifications can be conceived within the scope of the invention. For example the two picture signals may be delayed so as to compensate the deviation of the two images. However in this case the construction of the correction circuits would become somewhat complicated. Further in order to remove the pseudo-defects which might appear in the vicinity of the pattern contours use may be made of a circuit which comprises a contour signal producing circuit for generating a contour signal representing a contour region of a given width and a control circuit which decreases a defect detection sensitivity in accordance with the contour signal. By means of such a circuit any small defects in a region other than the contour regions can be effectively detected. Such a pseudo-defect removing circuit has been disclosed in the copending U.S. Ser. No. 922,217 filed July 5, 1978.

In the embodiment shown in FIG. 6 a flying spot cathode ray tube is provided for scanning the patterns in the raster mode, but use may be made of a line scanning device such as a laser scanner with a reflection mirror, or a solid statge linewise image senser. In such a case in order to effect the two dimensional scan and patterns and the scanning device have to be relatively moved in the direction perpendicular to the line scanning direction.

Further in the embodiment illustrated in FIG. 16 cascade connected one-shot multivibrators are provided so as to produce the gate pulses which divide the horizontal scanning period into the fractional periods of the equal duration. However these gate pulses may be generated by any one of various known circuits. Moreover it is not always necessary to produce the gate pulses which divide equally the horizontal scanning period.

What is claimed is:

1. An apparatus for detecting defects in patterns, particularly defects in chip patterns of photomasks for use in manufacturing semiconductor integrated circuits comprising optically scanning means including first and second lens systems each of which projects a scanning light spot onto a respective one of two identical portions of two patterns to be compared with each other and for scanning simultaneously said portions in a two dimensional scanning mode to produce first and second picture signals corresponding to said two identical pattern portions, respectively;

delay means for delaying at least one of said first and second picture signals for a delay time which is varied as a function of a position on the two dimensional scanning plane so as to decrease a relative deviation of the picture signals mainly due to a difference in distortion and/or magnification between the first and second lens systems; and means for receiving output picture signals from said delay means and forming a difference between these picture signals to produce a defect signal.

2. An apparatus according to claim 1, wherein said delay means comprise a variable delay circuit and a control circuit which supplies to the variable delay circuit a delay time control signal which varies as a function of a position on the two dimensional scanning plane.

3. An apparatus according to claim 2, wherein said variable delay circuit comprises a pi-type circuit network including inductors and variable capacitance diodes and said delay time control signal is applied to the variable capacitance diodes as a control voltage signal.

4. An apparatus according to claim 2, wherein said control circuit produces the delay time control signal having a repetition period equal to a horizontal scanning period so as to correct the deviation in the horizontal direction.

5. An apparatus according to claim 3, wherein said variable delay circuit comprises a picture input terminal for receiving the picture signal to be delayed;

a plurality of delay elements connected to said picture signal input terminal and each having a fixed delay time equal to a fraction of the horizontal scanning period;

a plurality of gates having respective picture signal input terminals connected to a respective one of said picture signal input terminal and the output terminals of the delay elements, respective output terminals and respective control input terminals;

a picture signal output terminal commonly connected to output terminals of said gates to produce the delayed picture signal; and gate pulse producing means for receiving the delay time control signal and supplying gate pulses to said control input terminals of given gates which should be made conductive in accordance with an amplitude of the delay time control signal.

6. An apparatus according to claim 5, wherein said gate pulse producing means comprises an analog to digital converter for converting the analog delay time control signal from the control circuit into a digital signal; and a decoder for decoding said digital signal to produce an output signal at a given one of a plurality of output terminals.

7. An apparatus according to claim 6, wherein said delay time control signal is of a substantially parabolic waveform having a period equal to the horizontal scanning period so as to correct the deviation in the horizontal direction due to the difference in distortion between the two lens systems.

8. An apparatus according to claim 5, wherein said delay time control signal is of a substantially sawtooth waveform having a repetition period equal to the horizontal scanning period so as to correct the deviation in the horizontal direction due to the difference in magnification between the two lens systems.

9. An apparatus according to claim 7, wherein said delay time control signal further includes in superimposition thereon a substantially sawtooth waveform having a repetition period equal to the horizontal scanning period so as to correct the deviation in the horizontal direction due to the difference in distortion and magnification between the two lens systems.

10. An apparatus according to claim 4, wherein said variable delay circuit comprises a picture signal input terminal for receiving the picture signal to be delayed;

a plurality of delay elements connected to the picture signal input terminal and each having a delay time equal to a fraction of the horizontal scanning period;

a plurality of gates having respective picture signal input terminals each connected to a respective one of the picture signal input terminal and output terminals of the delay elements, respective output terminals and respective control input terminals;

an output terminal commonly connected to the output terminals of the gates; and gate pulse producing means for receiving the delay time control signal and producing gate pulses at a plurality of output terminals which pulses divide the horizontal scanning period into a plurality of fractional periods, the control input terminals of given gates being fixedly connected to the output terminals of the gate pulse producing means so as to obtain at said output terminal a picture signal which has been desirably delayed.

11. An apparatus according to claim 10, wherein said gate pulse producing means comprises a plurality of cascade connected multivibrators to which is supplied the delay time control signal as a trigger pulse having a repetition period of the horizontal scanning period.

12. An apparatus according to claim 2, wherein said delay time control signal has a repetition period equal to a vertical scanning period of the two dimensional scan so as to correct the deviation in the vertical direction.

13. An apparatus according to claim 12, wherein said variable delay circuit comprises an input terminal for receiving the picture signal to be delayed;

a plurality of delay elements connected to said input terminal and each having a delay time equal to an integer multiple of the horizontal scanning period;

a plurality of gates having input terminals each connected to a respective one of said picture signal input terminal and output terminals of said delay elements, respective output terminals and respective control signal input terminals;

a picture signal output terminal commonly connected to the output terminals of the gates; and gate pulse producing means for receiving the delay time control signal and supplying gate pulses to given gates which sould be made conductive in accordance with the amplitude of the delay time control signal.

14. An apparatus according to claim 13, wherein said gate pulse producing means comprise an analog to digital converter for converting the analog delay time control signal into a digital signal, and a decoder for receiving the digital signal and producing an output signal at a given one of a plurality of output terminals.

15. An apparatus according to claim 13, wherein said delay time control signal is of a sawtooth waveform having a period of the horizontal scanning period and having an amplitude which varies during the vertical scanning period so as to correct the deviation in the vertical direction due to the difference in distortion between the two lens systems.

16. An apparatus according to claim 13, wherein said delay time control signal is of a substantially sawtooth waveform having a period equal to the vertical scanning period so as to correct the deviation in the vertical direction due to the difference in magnification between the two lens systems.

17. An apparatus according to claim 15, wherein said delay time control signal further includes in superimposed thereon a substantially sawtooth waveform having a period equal to the vertical scanning period so as to correct the deviation in the vertical direction due to the difference in distortion and magnification between the two lens systems.

18. An apparatus according to any one of the preceding claims 1 to 17, wherein said optically scanning means comprises a carrier table on which is placed a specimen having a number of identical patterns and two identical portions of two patterns in the specimen are scanned simultaneously.

19. An apparatus according to claim 18, wherein said optically scanning means comprises a flying spot cathode ray tube for producing a raster scanning light spot and said two lens systems project simultaneously images of said scanning light spot onto the identical portions of the patterns.

20. An apparatus according to claim 1, wherein said defect signal producing means comprises a circuit for removing a pseudo-defect appearing in a vicinity of pattern contours.

21. An apparatus according to claim 20, wherein said pseudo-defect removing circuit comprises a delay circuit for delaying the defect signal and an AND gate for receiving the delayed and non-delayed defect signals.

22. An apparatus according to claim 20, wherein said pseudo-defect removing circuit comprises a circuit for producing a contour signal which represents a contour region having a given width and a control circuit for receiving said contour signal to decrease a defect detection sensitivity in said contour region.

* * * * *